(12) United States Patent
Auradou et al.

(10) Patent No.: US 8,844,339 B2
(45) Date of Patent: Sep. 30, 2014

(54) DEVICE AND METHOD FOR MEASURING THE VISCOSITY OF A FLUID

(75) Inventors: Harold Roland Bernard Auradou, Palaiseau (FR); Jean-Pierre François Hulin, Saint-Maur-des-Fosses (FR); Benoît Bernard Joseph Semin, Vaudreching (FR)

(73) Assignee: Centre National de la Recherche Scientifique, Paris (FR)

( * ) Notice: Subject to any disclaimer, the term of this patent is extended or adjusted under 35 U.S.C. 154(b) by 539 days.

(21) Appl. No.: 13/123,572

(22) PCT Filed: Oct. 15, 2009

(86) PCT No.: PCT/FR2009/001210
§ 371 (c)(1),
(2), (4) Date: Jun. 20, 2011

(87) PCT Pub. No.: WO2010/043788
PCT Pub. Date: Apr. 22, 2010

(65) Prior Publication Data
US 2011/0239744 A1    Oct. 6, 2011

(30) Foreign Application Priority Data
Oct. 15, 2008 (FR) ...................................... 08 05718

(51) Int. Cl.
*G01N 11/04* (2006.01)

(52) U.S. Cl.
USPC .......................... 73/54.04; 73/54.37; 73/54.39

(58) Field of Classification Search
USPC .......................... 73/54.04, 54.23, 54.37, 54.39
See application file for complete search history.

(56) References Cited

U.S. PATENT DOCUMENTS

| 3,285,058 A | 11/1966 | Ostroot |
| 4,571,989 A * | 2/1986 | Dealy .......................... 73/54.39 |
| 4,750,351 A | 6/1988 | Ball |

(Continued)

FOREIGN PATENT DOCUMENTS

| EP | 1 674 865 | 6/2006 |
| EP | 1 927 842 | 6/2008 |
| GB | 2 129 144 | 5/1984 |
| WO | 98/38477 | 9/1998 |

OTHER PUBLICATIONS

Richou et al., "Draf force on . . . (numerical and experimental)", Chemical Engineering Science, vol. 60, 2005, pp. 2535-2543, XP002530819.
D'Angelo et al., "Single fiber . . . of the fluid rheology" Physics. Flu-Dyn, Sep. 2, 2008, pp. 1-12, XP002530820.

(Continued)

*Primary Examiner* — Hezron E Williams
*Assistant Examiner* — Paul West
(74) *Attorney, Agent, or Firm* — Clark & Brody

(57) ABSTRACT

The invention relates to a method for measuring the viscosity of a fluid, said method comprising the following steps: (a) providing a flow of said fluid in a laminar state inside a channel (14, 24) having a characteristic transverse dimension D, and in which an elongate member (12, 22) having a characteristic dimension d is placed substantially along the longitudinal direction of said channel and substantially at the center of the channel, and has a portion of the length l thereof submerged in said channel; (b) measuring the friction force (f) applied by said fluid on the walls of the elongate member; and (c) calculating the dynamic viscosity ($\eta$) of said fluid based on the equation (1) $f = \lambda \eta l U$ where U is the average flow rate and $\lambda$ is a geometric factor.

14 Claims, 7 Drawing Sheets

(56) References Cited

U.S. PATENT DOCUMENTS

| | | | |
|---|---|---|---|
| 4,750,531 A | | 6/1988 | Juenkersfeld et al. |
| 5,115,669 A | * | 5/1992 | Fuller et al. .................. 73/54.39 |
| 5,172,585 A | * | 12/1992 | Gleissle ...................... 73/54.04 |
| 6,755,079 B1 | * | 6/2004 | Proett et al. ................ 73/152.18 |
| 2003/0033859 A1 | | 2/2003 | Schoeb et al. |

OTHER PUBLICATIONS

Hui Lieu et al., "On the translation . . . a long tube" Physics of Fluids, vol. 16, No. 4, Apr. 2004, pp. 998-1007; XP002530923.

Wei-Chih Wang et al., "Fluid viscosity . . . light scattering" Meas. Scie. Technology, vol. 10, 1999, pp. 316-322 XP002530933.

* cited by examiner

DEVICE AND METHOD FOR MEASURING THE VISCOSITY OF A FLUID

The present invention relates to a method of measuring the viscosity of a fluid, and also to a corresponding device.

Numerous viscosity meters are already known that are suitable for use in laboratories or indeed in industrial applications.

Falling-ball viscosity meters are known in which a ball is released in a tube containing the fluid, and its limit velocity is measured in order to deduce the viscosity of the fluid therefrom.

That viscosity meter enables relatively accurate measurements to be obtained. Nevertheless, it is not very accurate with low-viscosity fluids, such as water. Furthermore, in practice, that device can be used only in a laboratory. Finally, it is necessary to use a plurality of balls and tubes in order to cover a wide range of viscosities.

There also exist capillary viscosity meters that operate on the basis of a fluid flow being established along a capillary tube by exerting pressure. The viscosity of the fluid can be deduced from the volume flow rate, which depends both on the viscosity of the fluid and on the pressure.

Those viscosity meters lack accuracy when they are used for substances of viscosity that can vary over a large range.

Mention may also be made of rotary viscosity meters that serve to measure or to impose a stress on a known area (e.g. of conical, plane, or cylindrical shape) and to estimate the speed gradient between the two surfaces (gradient assumed to be constant) on the basis of a speed of rotation that is either imposed or measured.

That viscosity meter is based on using a rotary vessel or moving body. The mechanical parts that are intended to move need to be made and positioned accurately and they require rotary devices to be used that present very low friction, and that are expensive.

Vibrating viscosity meters have an active portion that is a vibrating rod. They enable the amplitude of the vibration to be measured, which amplitude varies as a function of the viscosity of the fluid.

Furthermore, and in general, the above viscosity meters are used essentially in laboratories and are poorly adapted to industrial applications and/or to performing measurements continuously. They are also apparatuses of high cost price because of the tolerances required for their component mechanical parts. They are thus appliances that require very thorough maintenance, in particular when viscosity measurements are to be performed on fluids that are likely to damage them. Furthermore, they generally enable measurements to be obtained with sufficient accuracy only over a limited range of viscosities.

Mention may also be made of document U.S. Pat. No. 4,750,351, which describes a viscosity meter using a differential pressure measurement between the inlet and the outlet of a tube having a gas flowing therealong.

The flow of gas inside the tube is not laminar in the inlet portion of the tube, thereby disturbing the measurement, and thus considerably reducing the accuracy of the viscosity meter.

Document U.S. Pat. No. 6,755,079 describes a viscosity meter that also uses a differential pressure measurement between the inlet and the outlet of a tube in which a fluid flows.

Given the structure of the viscosity meter, the fluid can flow in one direction only. Furthermore, that document states that the Reynolds number is greater than 2000. The flow of fluid in the tube cannot be laminar for a large Reynolds number, thus once more reducing the accuracy of the viscosity meter.

Finally, document WO 98/38477 describes an appliance for measuring the apparent viscosity of particles in suspension in a medium. That appliance has a blade that is movable between a retracted position inside the appliance and a deployed position. In the deployed position, the blade is placed in the pipe, within which the medium flows and for which the flow direction is fixed. The appliance measures the shear force exerted on the blade.

Nevertheless, the characteristics of the flow differ from the walls of the pipe towards the center thereof. Thus, the shear force varies along the blade, and the appliance gives a value of low accuracy for the viscosity of the medium. That appliance is designed essentially to determine high viscosity.

An object of the invention is to mitigate those drawbacks by proposing a method of measuring the viscosity of a fluid that can be implemented on fluids of viscosities lying in a very broad range, and in particular fluids of viscosity that is low, with the measurement being performed with accuracy that is acceptable, being of percentage order, which method can be used equally well with newtonian fluids and with non-newtonian fluids.

The invention also provides a viscosity meter implementing the method. The viscosity meter is of low cost, in particular because its component parts do not require very accurate tolerances, and it can be used equally well in a laboratory or in an industrial setting.

Thus, the invention provides a method of measuring the viscosity of a fluid, the method comprising the following steps:

a) establishing a flow of said fluid under laminar conditions inside a channel of characteristic transverse dimensions D, an elongate element of characteristic dimension d being placed in said channel substantially along its longitudinal direction and substantially at its center, a fraction l of the length of the elongate element being immersed in said channel;

b) measuring the friction force f exerted by said fluid on the walls of said elongate element;

c) calculating the dynamic viscosity η of said fluid using the following equation:

$$f = \lambda \eta l U \quad (1)$$

where:

U is the mean speed of the flow; and

λ is a geometrical factor.

Throughout the description, the term "elongate element" is used to designate an element presenting a length l' and a diameter d, and having an immersed fraction that presents a length l, the ratio l/d lying in the range 10 to 100.

The method thus consists in establishing a laminar flow in a confined geometry, the flow thus being dominated by the viscosity and not by the inertia of the fluid, with this applying over a wide range of flow rates.

Furthermore, the method does not require any moving parts, whether moving in rotation or in vibration. The method is thus necessarily of implementation that is simplified compared with conventional methods of measuring viscosity.

Another technique for measuring viscosity consists in implementing steps b) to c) in succession with different positions of said elongate element in said channel, along the characteristic transverse dimension D, providing the ratio D/d is large enough, typically greater than 5 when the channel of the viscosity meter is cylindrical.

This enables the friction force f and the dynamic viscosity to be measured as a function of the position of the elongate element along the transverse dimension of the channel, and thus as a function of the speed profile of the flow. For the same mean speed, viscosity can then be determined for different shear rates.

When the fluid is newtonian, steps a) to c) may be implemented using a single value for the mean flow speed U, while nevertheless obtaining a measurement of the viscosity that presents appropriate accuracy.

When the fluid is non-newtonian, steps a) to c) are implemented in succession with different values of the mean flow speed U.

The method then consists in providing a curve of viscosity as a function of the mean flow speed, which curve can subsequently be analyzed usefully to determine the characteristics of the fluid.

When the fluid is non-newtonian and for a ratio D/d that is sufficiently large, typically greater than 5 when the channel of the viscosity meter is cylindrical, the method is advantageously implemented in such a manner as to obtain a curve of viscosity as a function of the mean flow speed for different positions of the elongate element along the transverse dimension of the channel, the flow rate being fixed or for differing flow rates, the position of the elongate element being fixed.

The method of the invention may advantageously be implemented continuously.

The invention also provides a viscosity meter implementing the measurement method of the invention, the viscosity meter comprising:

a channel of characteristic opening D and of length L;

an elongate element of characteristic dimension d and having an immersed fraction of length said element being placed in said channel in such a manner as to extend substantially along the longitudinal direction of said channel, substantially at the center of the channel; and measurement means for measuring the friction force f exerted on the walls of said elongate element when a fluid flow is established in said channel.

The viscosity meter of the invention may also include means for moving the elongate element in translation in the opening of the channel in order to measure variations in the friction force with varying position of said element along the transverse dimension.

Said elongate element may be flexible. By virtue of being flexible, the elongate element can easily align itself with the longitudinal direction of said channel under the effect of the fluid flow.

By way of example, mention may be made of filaments of polyester, rubber, or nylon.

The viscosity meter may include an imposed flow rate pump for causing the fluid to flow.

In a first variant of the viscosity meter, the channel is defined by the empty space between two substantially parallel plates.

In a second variant, the channel is defined by a cylindrical vessel.

Given the low costs of fabricating the viscosity meter of the invention, the channel and the elongate element may be for single use. This makes it possible to omit cleaning operations after performing measurement operations. This may also be extremely useful in the medical field, for example when the viscosity meter of the invention is used for measuring the viscosity of a sample of blood.

The invention can be better understood and other objects, advantages, and characteristics thereof appear more clearly on reading the following description, which is made with reference to the accompanying drawings, in which.

Figure 11:
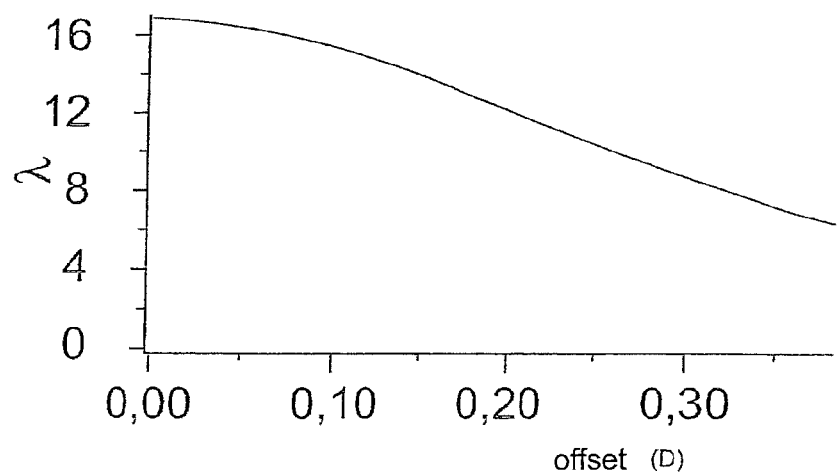
Figure 6:
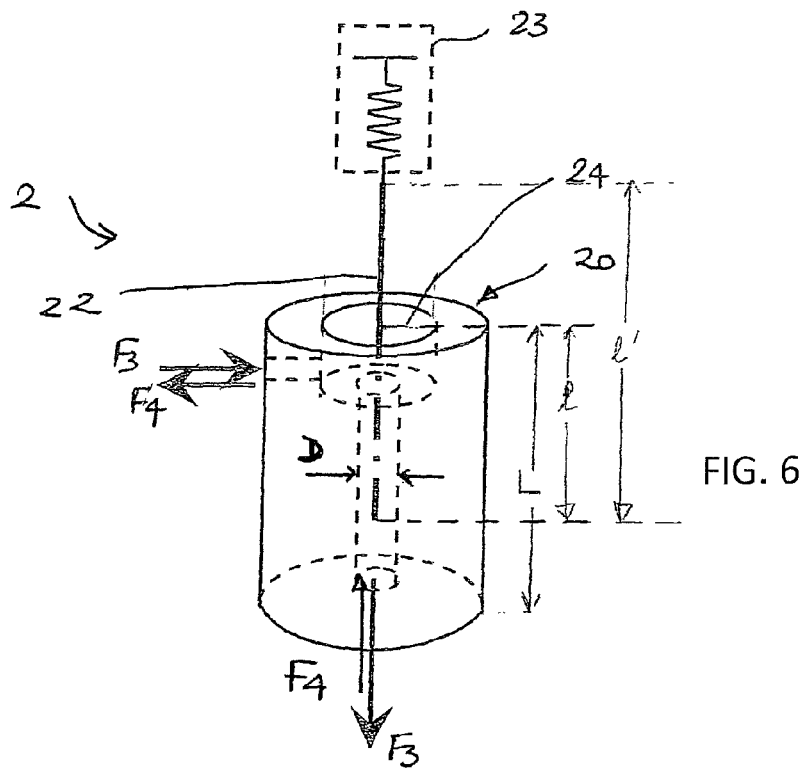
FIG. 6 is a diagrammatic perspective view of another example viscosity meter of the invention.
Figure 9:
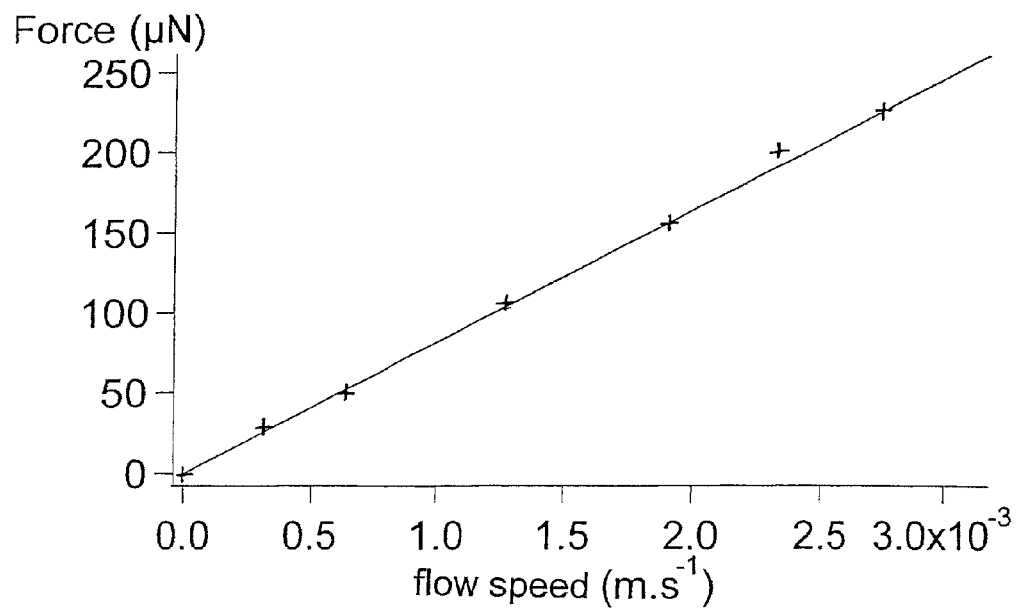
FIG. 9 is a curve showing the variation in the force (in $\mu$m) exerted on the elongate element of the viscosity meter shown in FIG. 6 as a function of the flow speed (in m·s$^{-1}$) when the element is a metal cylinder having a diameter equal to 1 mm, the fluid being a (15%/85%) water/glycerol mixture)
Figure 10:
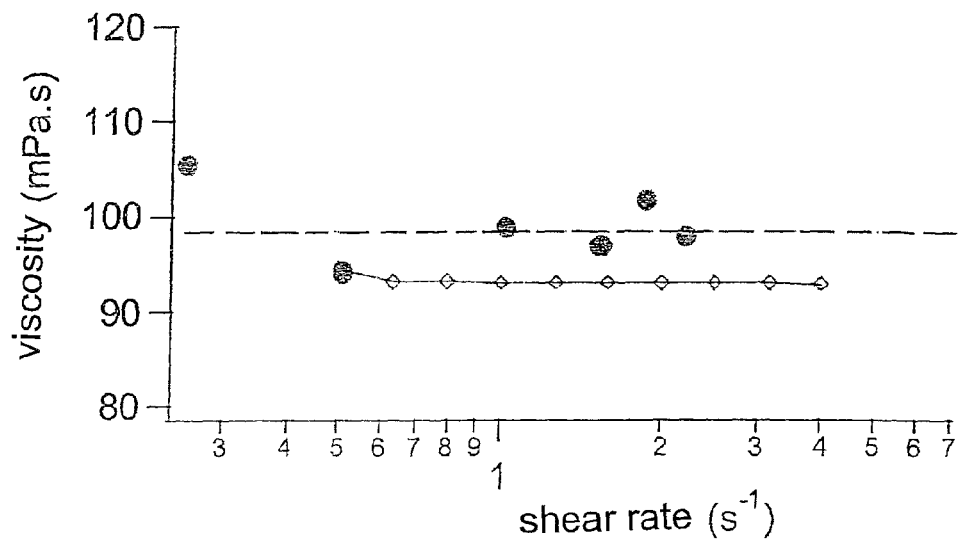
Figure 12:
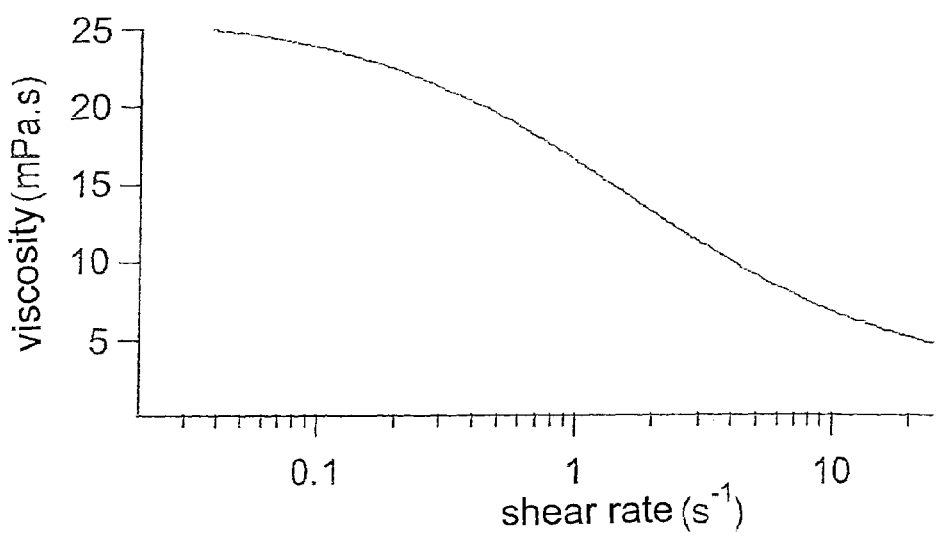
Figure 13:
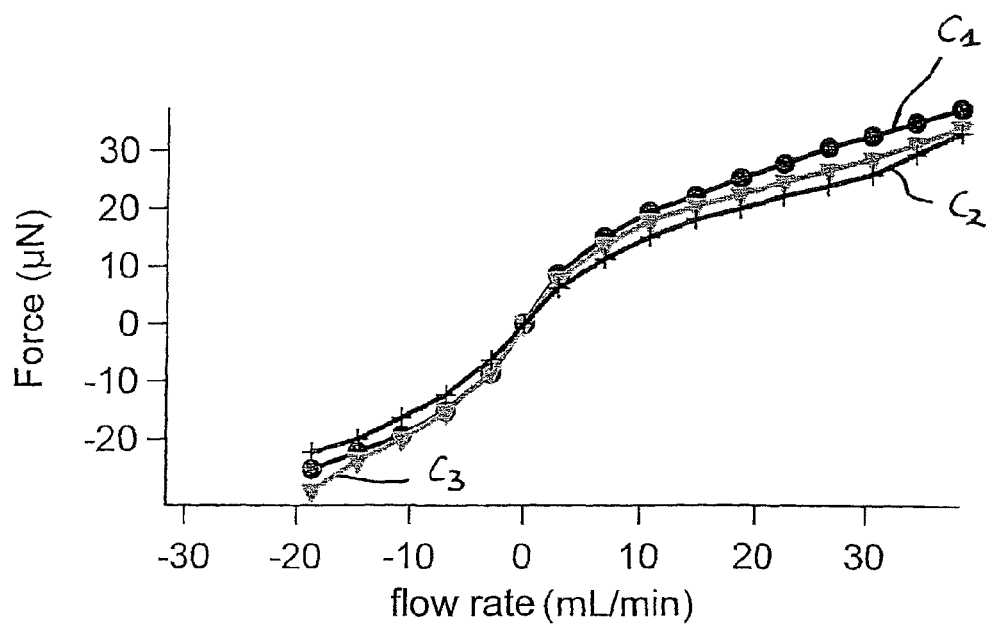

FIG. 10 plots, as a function of shear rate (in s$^{-1}$), viscosity values (mPa·s) of the (15%/85%) water/glycerol mixture obtained with the viscosity meter shown in FIG. 6 and corresponding to the results of FIG. 9 (•points) and the values obtained with an Anton Paar MCR501 rheometer (0 points), the dashed straight line representing a value from the literature;

FIG. 11 is a curve showing the geometrical factor $\lambda$ as a function of the offset of a cylindrical element in a viscosity meter having a channel defined by a tube (or as a function of the position of said element relative to the center of the tube), for D/d=5, the offset being expressed as a function of D;

FIG. 12 is a curve showing variation in viscosity (in mPa·s) as a function of shear rate (in s$^{-1}$) for a non-newtonian fluid, as obtained by a low-shear viscosity meter; and FIG. 13 plots three curves $C_1$, $C_2$, and $C_3$ showing variation in the force (in $\mu$N) as a function of the flow rate (in mL/min), where $C_1$ corresponds to the results shown in FIG. 12 and shows the theoretical equivalent force obtained from the rheological curve of fluid flowing in the viscosity meter, and $C_2$ and $C_3$ correspond to tests performed using the viscosity meter shown in FIG. 6 and for the same non-newtonian fluid.

Figure 1:
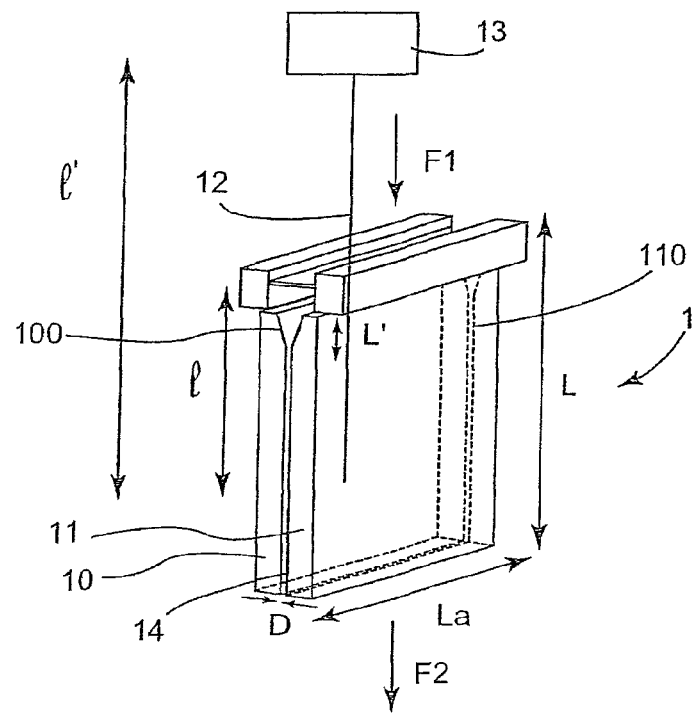
FIG. 1 is a diagrammatic perspective view of an example viscosity meter of the invention.

The viscosity meter 1 shown diagrammatically in FIG. 1 comprises two plates 10 and 11 that are substantially identical. These plates present facing surfaces 100 and 110 that are substantially smooth and parallel, except at the ends. In this zone, a Y-shape has been selected to facilitate putting the elongate element into place. This zone could advantageously be omitted or changed in shape.

These two facing faces define a channel 14 used for passing a fluid flow. They are spaced apart by a distance D referred to as the characteristic opening or transverse dimension of the channel.

The viscosity meter shown in FIG. 1 also includes an elongate element, here in the form of a wire 12. As shown in FIG. 1, the elongate element 12 presents a length l', with a fraction l of this length being placed in the channel 14 defined by the plates 10 and 11. Naturally, when the element 12 is completely immersed in the liquid, then l=l'.

The element 12 is placed substantially at the center of the channel 14, thereby excluding any contact between said element and the walls of the channel.

The plates present a length L that may be measured from the level of the fluid. If the length L' of the channel inlet is sufficiently short relative to the length L of the channel 14, and if L' is sufficiently short compared with the fraction l of the element that is immersed, then inlet effects are negligible. For the viscosity meter shown in FIG. 1, the second condition is satisfied in particular when L'<0.3 l.

The elongate element 12 is connected to a force sensor 13. The connection is made in such a manner that the measured force is the real force exerted on the walls of the elongate element.

The assembly is placed on a movement table (not shown in FIG. 1) that serves to move the elongate element in the opening and along the transverse dimension D. Force can thus be measured for different locations in the characteristic opening of the channel.

The elongate element may take various shapes, in particular that of a cylinder, e.g. made of glass or of metal, or it may even be in the form of twisted strands.

As a general rule, there is no need to have a flow of fluid inside the tube.

It is considered that the section of this element presents a characteristic transverse dimension d, that corresponds to its diameter if it is a cylinder, or indeed to the greatest dimension in its cross-section, if its section is not regular, as applies to twisted strands.

Means that are not shown in FIG. 1 serve to cause a fluid to circulate in said channel along arrows F1 and F2 shown in FIG. 1, the flow of fluid being under laminar conditions. The flow direction may be reversed.

The characteristic dimensions D and d of the channel 14 defined by the plates and the elongate element 12 are selected in such a manner that the ratio D/d is less than or equal to 100.

The device shown in FIG. 1 then defines a so-called "confined" geometry. As a result, the laminar flow of fluid in the channel 14 depends essentially on the viscosity of the fluid and not on its inertia. Thus, when a flow of fluid under laminar conditions is established in a confined geometry, there exists a simple equation between the viscosity of the fluid and the viscous friction force exerted on the elongate element placed in a flow of said fluid. This equation is as follows:

$$f = \mu \eta l U \quad (1)$$

where:
 f is the force exerted on the elongate element;
 U is the mean speed of the flow (spatial mean of the speed over the dimension D);
 η is the viscosity; and
 λ is a geometrical factor that may be determined accurately, either by numerical simulation or by calibration.

When the end effects are negligible and for ratios D/d<5, the geometrical factor λ varies in approximately affine manner with the ratio d/D. When the element is also at the center of the channel, i.e. on the plane of symmetry of the channel, parallel to the plates 10 and 11, then λ follows the following equation (observed numerically and experimentally):

$$\lambda = 2.1 + 13.8 d/D$$

Equation (1) is valid for a newtonian fluid, i.e. a fluid having constant viscosity. It is explained below how a non-newtonian fluid can be analyzed using the same equation.

Furthermore, it is necessary for l/D to be sufficiently large (>5, for example) in order to be able to assume that the flow is two-dimensional and that λ is independent of D. For a newtonian fluid and for small Reynolds numbers (Re<0.1), and if proceeding with calibration of the device, this condition is not necessary.

It is recalled here that Reynolds number Re is defined by the following equation:

$$Re = \frac{\rho U d}{\eta} \quad (2)$$

where:
 ρ is the density of the fluid (mass per unit volume);
 η is the dynamic viscosity of the fluid;
 U is the mean flow speed; and
 D is the characteristic dimension of the opening of the channel in which the fluid flows.

Before examining experimentally-obtained results in greater detail, it is appropriate to recall that Reynolds number serves to determine which effects dominate a fluid flow, namely inertial effects or viscous effects.

When Reynolds number is less than 20, it can be assumed that the inertial effects appearing in the flow are negligible. Thus, the flow is dominated by viscous effects and the force exerted on the elongate element placed in the flow presents behavior that is linear relative to the mean flow speed of the fluid.

It can also be assumed that the method of the invention makes it possible to obtain information that is of interest when Reynolds number values are less than 50. In general, it is possible to determine experimentally the maximum Reynolds number (and thus maximum flow rate) for which inertial effects can continue to be ignored.

Figure 2:
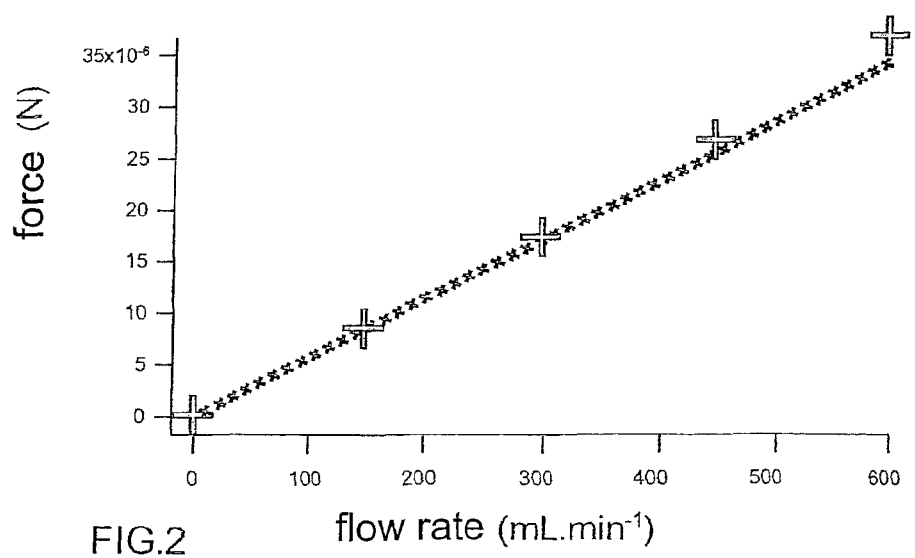
FIG. 2 is a curve plotting the force (in newtons (N)) exerted on the elongate element used in the viscosity meter shown in FIG. 1 as a function of the flow rate of the fluid (in milliliters per minute (mL·min$^{-1}$)) when the elongate element is a glass cylinder of diameter equal to 1.5 millimeters (mm) and the fluid is water.

Reference is now made to FIG. 2, which shows experimental results obtained using the viscosity meter shown in FIG. 1, presenting a characteristic dimension D equal to 5 mm, and having a glass cylinder of diameter d equal to 1.5 mm placed therein. The glass cylinder was placed at the center of the channel 14 defined between the plates 10 and 11. The fluid used was water.

The force sensor 13 measured the hydrodynamic force exerted on the elongate element.

FIG. 2 plots measurement points (+) for the force exerted on the cylinder, expressed in newtons, as a function of the fluid flow rate, which is proportional to the fluid speed, and it applies to tests that were performed with distilled water at a temperature of 20.0° C.

The curve plotted as a dotted line corresponds to a linear regression based on the initial measurement points (lowest flow rates).

This curve confirms that the variation of the force as a function of flow rate is indeed linear. The slope of the straight line serves to determine the viscosity.

For the curve shown in FIG. 2, the measured viscosity is 1.1 mPa·s.

The measurement point corresponding to a flow rate greater than 500 mL·min$^{-1}$ departs from the dotted-line curve that corresponds to the linear regression.

This confirms that inertial effects cease to be negligible at high flow rates. By way of indication, for a flow rate of 300 mL·min$^{-1}$ and in the viscosity meter that was used, the Reynolds number is already about 50.

Naturally, given the definition of the Reynolds number, these inertial effects can be reduced if the characteristic dimension D of the measurement device is also reduced.

Figure 3:
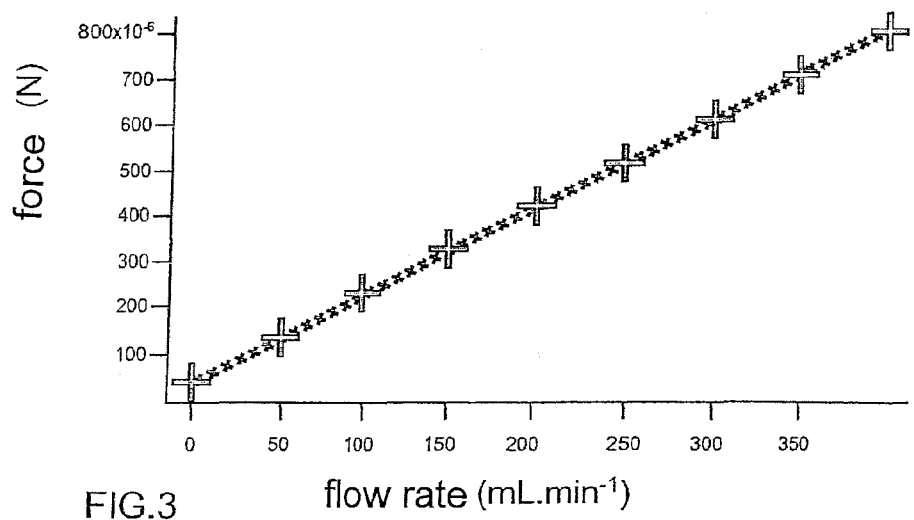
FIG. 3 is a curve plotting the force (in N) exerted on a copper cylinder having a diameter of 2 mm placed in the device shown in FIG. 1, as a function of flow rate (in mL·min$^{-1}$), when the fluid is a (25%/75%) water/glycerol mixture.

FIG. 3 shows experimental results obtained with the viscosity meter shown in FIG. 1, having placed therein a copper cylinder with a diameter d equal to 2 mm. The copper cylinder was placed substantially centered in the channel 14, the characteristic dimension D of the device then being equal to 5 mm. The fluid used was a mixture of water and glycerol (a newtonian fluid), with the glycerol fraction being about 75% by weight, and the temperature was 21.9° C.

The measurement points are represented by crosses (+), and the dotted black line corresponds to a linear fit to the curve.

Once more, it can be seen that the force varies linearly with flow rate, the slope of the straight line serving to determine viscosity. The measured viscosity value is 35.2 mPa·s.

FIG. 3 shows that in that experiment, the measurement points did not depart from the linear regression curve, even at high flow rate.

In practice, in that experiment, Reynolds number was always less than 5.

The result shown in FIGS. 2 and 3 show that regardless of the newtonian fluid (such as water or ordinary oil) that is used, linear variation is indeed observed in the force exerted on the tube with varying flow rate.

Thus, for such fluids and as shown in FIGS. 2 and 3, a single measurement at a given flow rate suffices to obtain the value for the viscosity of the fluid. The value of the force as measured is proportional to the flow rate so long as the viscosity effect is dominant compared with inertial effects.

The fact that equation (1) is linear for a newtonian fluid implies that it remains true even if the flow rate or the flow speed is not constant over time. It then suffices to replace the speed and the force in equation (1) by their mean values over time.

The device of the invention thus makes it possible to measure the viscosity of a newtonian fluid, even if the flow rate through the device is not constant. This may occur in particular with pulsed flows, or indeed with flows that are produced using peristaltic pumps.

Figure 4:
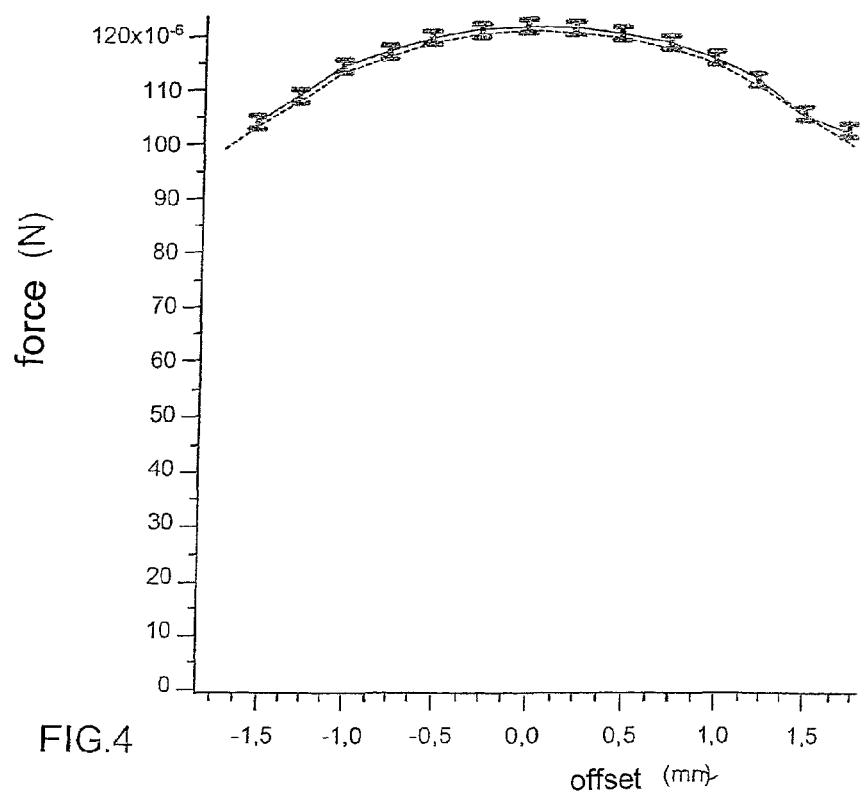
FIG. 4 is a curve showing the force (in N) exerted on a glass cylinder having a diameter of 1.5 mm placed in the FIG. 1 device, as a function of its offset (or its position relative to the plane of symmetry of the channel of the device)

Reference is now made to FIG. 4, which relates to other experimental results that have been obtained to show the influence of the position of the elongate element in the channel of the device shown in FIG. 1.

Thus, FIG. 4 gives measurement points (represented by gray bars (I)) for the force exerted on a glass tube having a diameter d of 1.5 mm placed in the channel 14 of the device 1 with a characteristic dimension D equal to mm, with its position being measured relative to the plane of symmetry of the channel, i.e. the plane situated at equal distance from both plates 10 and 11. The distance between the tube and the center of the channel, or indeed the offset of the tube, may vary over the range −1.75 mm to +1.75 mm.

The measurements were performed using a fluid made up of a mixture of water and glycerol, the glycerol concentration being 75.7% by weight and the temperature being 21.4° C.

The gray vertical bars shown in FIG. 4 give the maximum dispersion for the measurements taken, while the gray curve corresponds to the experimental measurements.

In FIG. 4, there can also be seen a dashed-line black curve that corresponds to viscosity values for the flow as calculated by numerical simulation. Starting from D, d, and the offset of the elongate element, it is possible (by numerical calculation) to calculate λ as a function of offset. Thereafter, equation (1) is used. The two curves are substantially superposed since they coincide to within 3%. In the example viscosity meter shown in FIG. 1, the width La of the plates or of the channel is 9 centimeters (cm) and the effect of the width is not taken into account in the digital calculation. This shows that so long as the width La is large relative to the dimension D of the channel, it is mainly the dimension D that dominates the measurement: the effect of the dimension La is then negligible.

Furthermore, over a range of 1.6 mm (from −0.8 mm to +0.8 mm), the measured force departs by less than 5% from the value at the center of the channel. This shows that the geometrical factor λ depends only little on the position of the tube in the channel, when the tube lies in the vicinity of the center of the channel, and also depends only little on any irregularities that might exist in the walls of the channel and of the tube.

Figure 5:
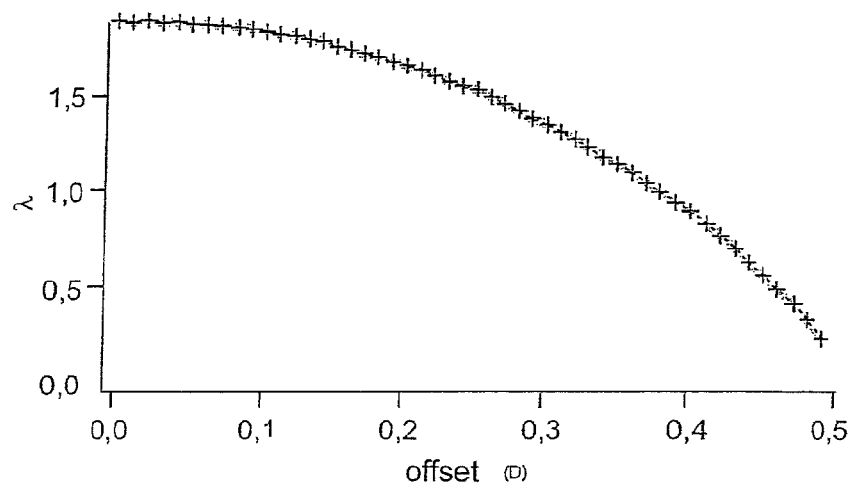
FIG. 5 is a curve determined by digital modeling showing the geometrical factor $\lambda$ as a function of the offset of a cylindrical element in a device as shown in FIG. 1 (or indeed as a function of the position of said element relative to the plane of symmetry of the channel of the device), for D/d=100, with the offset being expressed as a function of D.

FIG. 5 shows variations in the geometrical factor λ as a function of offset and for a ratio D/d=100. The geometrical factor λ is obtained by numerical modeling using a finite element model, as a function of the D-normalized offset of a cylindrical element (i.e. the distance between the longitudinal axis of the element and the plane of the symmetry of the walls given references 100 and 110 in FIG. 1). In this figure, this offset is made non-dimensional by using the distance D between the two walls. The offset is zero when the element is halfway between the walls and is at a maximum when the elongate element is touching one of the walls (the element is then in contact with the wall over its entire length). In this example, the maximum offset is:

$$\frac{D-d}{2d} \approx 0.5$$

For reasons of symmetry and as shown in FIG. 4, the geometrical factor (or friction force) does not depend on the sign of the offset. Thus, only positive offset values are given in FIG. 5.

These results show clearly that so long as the offset is less than ±0.1 D (i.e. ±10d), the geometrical factor varies little (less than 5% relative to its values at the center). This shows the robustness of the method in the face of inaccuracy concerning the centering of the elongate element. The measurement gives results that are reliable even for small inaccuracies of positioning.

For ratios D/d>5 and greater, the measurement becomes more and more sensitive to the speed profile in the opening of the channel. Variation in force measurement with movement in the opening can advantageously be used to obtain the variation of the viscosity as a function of shear rate.

This leads to several consequences.

Firstly, implementing the method of the invention with a device of the kind shown in FIG. 1 makes it possible to obtain measurements that are correct, without it being essential for the elongate element to be exactly centered in the channel.

Furthermore, the surface of the elongate element need not necessarily be very regular.

Thus, experiments have shown that it is even possible to make valid measurements with an elongate element made up of a plurality of single strands that are twisted together. Under such circumstances, the section of the elongate element is not circular. Nevertheless, the factor λ can be calculated accurately by using the mean diameter of the element.

In general, the surface state of the elongate element and of the walls of the channel does not require very accurate tolerances. This naturally has advantageous consequences in terms of the manufacturing cost of the viscosity meter of the invention.

Furthermore, experiments have been carried out that also show that the material from which the elongate element is made does not matter. In the results shown in FIGS. 2 and 3, the elongate element is made of glass or of copper. It is also possible to envisage using an elongate element made up of twisted polyester strands, such as sewing thread.

This also contributes to reducing the cost of fabricating the viscosity meter of the invention.

Reference is made to the table below (Table 1), which shows the accuracy that can be obtained by the method and the viscosity meter of the invention.

| Fluid used | Measured viscosity | Expected viscosity |
|---|---|---|
| Water (FIG. 2) | 1.1 mPa · s | 1.0 mPa · s |
| Mixture of water and 75.7% glycerol (FIG. 3) | 35.2 mPa · s | 34.5 mPa · s |
| Mixture of water and 52.3% glycerol (FIG. 4) | 6.7 mPa · s | 6.5 mPa · s |

For each of the fluids used, Table 1 gives the viscosity measured by using the method and the viscosity meter of the invention, in accordance with the experimental results that appear in FIGS. 2 to 4. The table also gives the viscosity value obtained from tables and measurements of the densities and the temperatures of the fluids used. As an indication, such tables may be available at the following address: http://www.dow.com/glycerine/resources/table18.htm A comparison between these values shows that the measured viscosity values are very close to the reference values. Furthermore, the uncertainty in these values does not vary over the range of viscosities under study. Other experiments have been carried out that confirm the observation that results from the above-described experiments.

Furthermore, force sensors are available on the market that enable forces to be measured over a very broad range. For example, mention may be of Sartorius CP 225 D balance that enable forces to be measured over the range $10^{-7}$ N to $8 \times 10^{-1}$ N, corresponding to apparent weights lying in the range $10^{-5}$ grams (g) to 80 g.

This contributes to enabling viscosity values to be measured over a large range with accuracy that is substantially constant.

Thus, compared with known viscosity meters, such as vibratory viscosity meters, the viscosity meter of the invention is capable of measuring viscosities that are very low, such as the viscosity of water.

It results from the above description that the viscosity meter of the invention does not have any mechanical moving parts, be those movements in rotation or in vibration. This also has consequences in terms of the fabrication cost of the viscosity meter insofar as parts that are stationary may be machined with less accuracy than parts that are in rotary or vibratory motion. Furthermore, any risk of breakdown is thus greatly limited.

In the example shown in FIG. 1, the viscosity meter is made from two facing plates that define a channel. It is also possible to envisage making a viscosity meter in which the channel is defined by a tube.

Thus, the viscosity meter 2 shown in FIG. 6 comprises a cylindrical vessel 20 defining a channel 24 for passing the flow of a fluid. The diameter D of the channel corresponds to the characteristic dimension of the channel.

The viscosity meter 2 also has an elongate element that is here constituted by a cylinder 22 of diameter or of characteristic dimension d. It presents a length l' having a fraction l immersed in the channel 24. The length L of the channel is always greater than l.

The elongate element is placed substantially at the center of the channel 24, thereby excluding any contact with the walls of the channel.

The element 22 is connected to a force sensor 23, here a precision balance, so that the force as measured is the real force exerted on the walls of the element.

Means (not shown) serve to cause a fluid to flow in the channel 24 along arrow $F_3$ corresponding to injecting fluid, or along arrow $F_4$ corresponding to sucking up fluid. Either way, the fluid flow takes place under laminar conditions.

As described above with reference to FIG. 1, the ratio D/d is less than or equal to 100.

By way of example, the diameter D of the channel is 1 cm, the diameter d of the cylinder is 1 mm, the length l' of the cylinder is 11 cm, and the immersed fraction l is 7 cm.

As explained above, so long as the inertial effects of the flow are negligible (Re<50, or even Re<20), the force f measured by the sensor 23 is defined by equation (1), thus making it possible to determine the viscosity of the fluid, once the geometrical factor λ has been determined.

This determination may be performed by calibration using a fluid of known viscosity, or else it may be performed numerically.

For numerical calculation, the speed field is calculated by solving Stokes' law (inertial effects are negligible here):

$$-\overrightarrow{\text{grad}}P + \eta \Delta \vec{V} = 0 \quad (3)$$

The speed of the flow varies only with radial distance r, measured from the longitudinal axis:

$$\eta \Delta V_z(r) = \frac{\partial P}{\partial z} = const = b \quad (4)$$

For a newtonian fluid, the analytic solution may be used to obtain Vz(r), since viscosity has a value that is constant.

For non-newtonian fluids, this 2D expression is solved iteratively using Freefem++ software in order to obtain the speed Vz(r). The viscosity then depends on the shear rate. This new constraint implies that on each iteration it is necessary to estimate the viscosity field.

The force acting on the elongate element is the sum of two contributions: a pressure force and a friction force. The general equation for the force f has the following form:

$$f = l_c \left[ \underbrace{\pi r^2 b}_{\text{pressure forces}} + \underbrace{\int_C \eta \left( \frac{\partial V_z}{\partial x} n_x + \frac{\partial V_z}{\partial y} n_y \right)}_{\text{friction forces}} \right] \quad (5)$$

The integral being calculated on the outline of the cylinder.

For a fluid of known viscosity, an imposed speed U, and a known length l, it suffices to calculate the force f: with the geometrical factor λ then being obtained by calculating the ratio f/ηUl.

Figure 7:
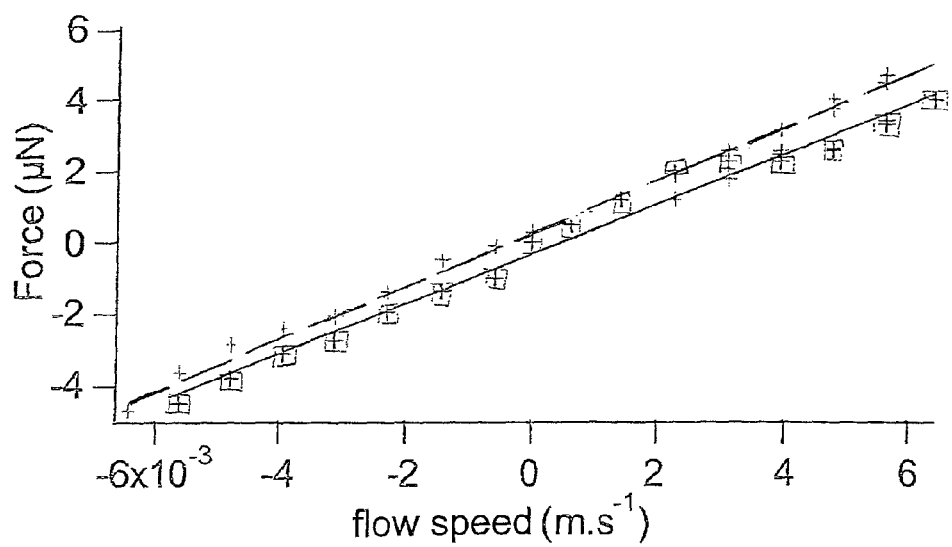
FIG. 7 is a curve plotting variation in the force (in micronewtons ($\mu$N)) exerted on the elongate element of the viscosity meter shown in FIG. 6, as a function of the flow speed (in meters per second (m·s$^{-1}$)) when the element is a metal cylinder having a diameter equal to 1 mm and the fluid is water.

Reference is made to FIG. 7 which shows experimental results obtained by using the viscosity meter shown in FIG. 6, presenting a characteristic dimension D equal to 1 cm and having placed therein a metal cylinder with a diameter d equal to 1 mm. The cylinder was placed at the center of the channel 24. The fluid used was water.

Under such conditions, the geometrical factor was estimated as being 9.9, in application of the above-described numerical method.

Tests were performed by varying the flow direction (injecting the fluid F3: positive speed; by sucking up the fluid F4: negative speed), and for two different fluid temperatures (22.6° C. and 22.8° C.).

The weight measured by the balance 23 serves to determine the hydrodynamic force exerted on the element 22.

FIG. 7 gives measurement points (+ for a temperature of 22.6° C. and ⊞ for a temperature of 22.8° C.) of the force expressed in μN as a function of the speed of the water (m·s$^{-1}$).

The curves (continuous line for the temperature of 22.8° C. and dashed line for the temperature of 22.6° C.) correspond to linear regressions.

Once more, these curves confirm that the variation of the force as a function of speed is indeed linear. The slope of the straight line and equation (1) enable the viscosity to be measured.

Thus, the measured viscosity is 0.982 mPa·s at 22.6° C. and 0.9238 mPa·s at 22.8° C. These measured values may be compared with the corresponding tabulated values (0.942 mPa·s at 22.6° C. and 0.937 mPa·s at 22.8° C.).

In order to obtain a better assessment of the accuracy of the values obtained using the viscosity meter of the invention, comparative measurements were undertaken with a rotary Contraves Low-shear 30 viscosity meter at the temperature of 22.6° C. The shear rate in the channel 24 was determined by using the following equation:

$$\dot{\gamma} = \frac{4Q}{\pi R^3} \quad (6)$$

with:
$\dot{\gamma}$: shear rate;
Q: volume flow rate applied in the cell;
R: cell radius.

Figure 8:
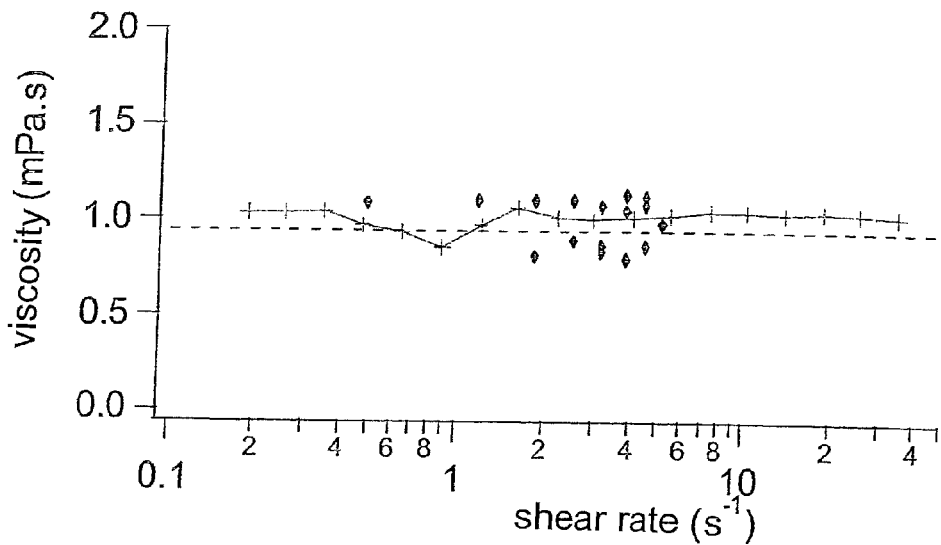
FIG. 8 shows the viscosity values (in millipascal-seconds (mPa·s)) of water obtained with the viscosity meter shown in FIG. 6 and corresponding to the results of FIG. 7 (♦-points) and the values obtained with a Contraves Low-shear 30 rotary viscosity meter (+ points) as a function of the shear rate (per second (s$^{-1}$))

FIG. 8 gives the values obtained for water viscosity using the viscosity meter of the invention (♦) and using the Contraves Low-shear 30 viscosity meter (+), as a function of shear rate.

The continuous curve joins the points corresponding to the Contraves Low-shear 30 viscosity meter.

Furthermore, the straight dashed line gives the tabulated value for water viscosity which is 0.942 mPa·s at a temperature of 22.6° C.

FIG. 8 shows that the measurement error concerning the viscosity of water when using the viscosity meter of the invention is small (no more than 10%) compared with the measurements obtained using the Low-shear viscosity meter, even though that viscosity meter is expensive and relatively complex to use. This measurement error could be reduced by achieving better control over temperature.

Other tests have been performed using the viscosity meter shown in FIG. 6 under the conditions set out in FIG. 7, with the fluid used being a mixture of glycerol and water having 85% by weight of glycerol.

The tabulated viscosity for that mixture at the measurement temperature (23° C.) is 98.4 mPa·s.

The forces obtained on the cylinder with that mixture are shown in detail in FIG. 9.

Once more, FIG. 9 shows that the variation in the force as a function of the speed of the flow is indeed linear. The slope of this straight line enables viscosity to be determined, and it is found to be 96.9 mPa·s.

A comparison with the tabulated value for the viscosity (98.4 mPa·s) shows that the viscosity value measured with the viscosity meter of the invention is very close to the reference value.

In order to better assess the accuracy of the values obtained with the viscosity meter of the invention, on the basis of forced values, dynamic viscosity was calculated using equation (1). These results have been compared with the tabulated value and with measurements performed using the Anton Paar MCR501 rheometer.

FIG. 10 gives the values for the viscosity of the mixture under consideration as obtained with the viscosity meter of the invention (• points) and with the MCR501 rheometer (◊ points) as a function of shear.

The continuous line curve joins the points corresponding to the MCR501 rheometer.

Furthermore, the straight dashed line illustrates the tabulated value for the viscosity of the mixture (98.4 mPa·s).

FIG. 10 shows that the viscosity meter of the invention makes it possible to obtain values that are close to the tabulated viscosity (on average to within 3% and at worst to within 7%). Concerning the measurements performed using the Anton Paar rheometer, they were 5% below the tabulated values.

This comparative test shows that the viscosity meter of the invention serves to determine the viscosity of the fluid with accuracy that is better than that of the Anton Paar rheometer. This observation should be even more marked for fluids of low viscosity.

An important consequence of the method of the invention is that it makes it possible to reduce the size of the viscosity meter considerably. This enables measurements to be taken on small volumes of fluid, without any consequence on the accuracy of the measured force value.

By dimensional analysis (and verified experimentally), it can be shown that the geometrical factor λ depends a priori on l/D, D/d, and on the ratio of the offset and D. In practice, if the ratio l/D is very large, e.g. greater than 50, then the geometrical factor λ depends little thereon. When the elongate element is placed between two parallel plates (as shown in FIG. 1), the variation in λ with offset is particularly small when the elongate element is placed close to the center of the plates. This point is illustrated in FIG. 4 which shows that for D/d=3 λ varies continuously as a function of offset, with a maximum at the center and with variation that is small (less than 5%).

This point is further demonstrated for D/d=100 in FIG. 5 that gives the variations in the geometrical factor λ as a function of offset. Over a wide range going from −0.1 D to 0.1 D, this factor varies by less than 5%. For this geometry, the offset has little effect on the measurement and λ is mainly a function of the ratio D/d, regardless of the offset. Consequently, poor positioning of the object has little effect on the measurement.

When the cylinder is placed in a tube, it is appropriate for the ratio D/d to be greater than 5 if it is desired that the force measured in the vicinity of the center depends little on the accuracy with which the elongate element is positioned.

This situation is shown in FIG. 11 which gives variations of λ for D/d=5 as a function of offset.

For reasons of symmetry and as in FIG. 5, only positive offset values are given in FIG. 11. The geometrical factor λ is obtained by numerical modeling using the finite-element method, as a function of the D-normalized offset of the cylindrical element. Here, the element is placed inside a tube or channel having a diameter D, the two axes being parallel and the diameter ratio being selected to be equal to D/d=5. In this situation, the offset corresponds to the distance between the longitudinal axis of the cylindrical element and the axis of symmetry of the tube. The offset is thus zero when the two axes coincide and its maximum value is reached when the elongate element touches the inside wall of the tube. Under such circumstances, the maximum offset normalized relative to the diameter D is:

$$\frac{D-d}{D} = 0.4$$

The geometrical factor and thus the force (which is proportional thereto) thus varies by less than 10% when the elongate element is at an offset of 0.1 D.

For a viscosity meter of the type shown in FIG. 1 that has a channel defined by parallel plates, once D/d>5 (situation in which force variations in the opening become greater than 5%), the force variations in the opening become appreciable. Measuring force variations as a function of the position of the element in the opening of the channel, along its transverse dimension, can then be advantageous in determining the rheological characteristics of the fluid as a function of the shear rate that varies across the opening.

When the element is centered, an important consequence is that, providing the mean flow speed (U), the length (l) of the immersed portion of the elongate element, and the ratio of the characteristic dimensions d/D all remain the same, and when the ratio l/D is greater than 50, the device can be miniaturized: such miniaturization has practically no consequence on the force values as measured.

For example, for a length l equal to 2 cm and a given speed U, the measured force f is practically the same for a cylinder of diameter d=1 mm in a tube of diameter D=2 mm and for a cylinder of diameter d=100 micrometers (μm) placed in a tube having a diameter D=200 μm. In contrast, the volume of fluid used for performing the measurement is decreased by a factor of 100.

This miniaturization is also made possible by the fact that the viscosity meter of the invention does not have any moving parts.

This further contributes to reducing the costs of fabricating a viscosity meter of the invention.

Furthermore, it is possible to envisage making viscosity meters of the invention with parts defining the channel for the fluid and an elongate element that are for single use only.

This can be particularly useful when the measurements are to be performed in fluids that are likely to damage the parts forming the channel and the elongate element placed therein. This advantage may also be extremely useful in the medical field, where it is often necessary to use single-use devices.

The above description relates essentially to newtonian fluids. Nevertheless, the method of the invention is also applicable to non-newtonian fluids.

With non-newtonian fluids, the force exerted on the elongate element of the viscosity meter varies in non-linear manner with the speed of the flow: the viscosity of the fluid depends on the shear rate.

For a non-newtonian fluid, the method is applied successively at different values for the speed of the flow, either by measuring the force while moving the elongate element in the opening of the channel without modifying the speed of the flow, or by measuring the force at different flow rates while maintaining the position of the elongate element stationary.

The speed involved is spatially averaged and a priori instantaneous in time. In any event, it is subsequently possible to take a time average if that makes the results easier to use. The viscosity meter then serves to provide a curve giving the variation in the measured force as a function of the flow rate, or as a function of position in the opening.

The information that is obtained may then be processed in conventional manner using known mathematical models.

Tests have been performed with an aqueous solution containing 250 parts per million (ppm) of scleroglucan, a neutral polysaccharide.

The rheological curve obtained with the Low-shear viscosity meter, as shown in FIG. 12, shows clearly the rheofluidizing nature of the fluid.

The measurement points (•) may be fitted using an equation for a Carreau-type fluid:

$$\eta = \frac{\eta_0 - \eta_\infty}{1 + \left(\frac{\dot{\gamma}}{\dot{\gamma}_0}\right)^{1-\alpha}} + \eta_\infty \quad (7)$$

where $\eta$, $\eta_o$, and $\eta_\infty$ represent respectively dynamic viscosity, viscosity on the newtonian plateau, and viscosity at a shear rate $\dot{\gamma}$ that is infinite. $\dot{\gamma}_0$ is the shear rate that corresponds to the transition between two flow regimes (newtonian plateau and power law regime). The values of these coefficients obtained by the Low-shear viscosity meter are given in Table 2.

| $\dot{\gamma}_0$ (s$^{-1}$) | $\eta_0$ (Pa·s) | $\eta_\infty$ (Pa·s) | α |
|---|---|---|---|
| 1.55 | 26 × 10$^{-3}$ | 2.78 × 10$^{-3}$ | 0.07 |

The rheological equation given by equation (6) was subsequently reinjected into the Freefem++ software to obtain a numerical estimate of the friction forces applied against the inside cylinder (cf. equation (5)).

Furthermore, two tests were performed, at the same temperature and using the same fluid, with the viscosity meter shown in FIG. 6, having an elongate element of diameter d equal to 1 mm and with an immersed fraction l of 7 cm.

FIG. 13 plots the curve $C_1$ ( • ) obtained from the rheological curve shown in FIG. 12, together with the curves $C_2$ (—+—) and $C_3$ (—*—) corresponding to tests performed using the viscosity meter of the invention.

A comparison between those three curves shows that the results obtained with the viscosity meter of the invention have good correlation with the force as calculated numerically using Freefem++. The maximum difference between the numerical values and the experimental values is 7%.

Thus, the viscosity meter of the invention enables measurements to be performed on fluids that are newtonian or non-newtonian at viscosities lying for example in the range less than 1 mPa·s to 100 mPa·s. By means of this system, it is easy to perform measurements continuously that are accurate and fast (requiring a few seconds).

Furthermore, the method of the invention has the advantage of being usable regardless of the size of the measurement channel or cell: the force is proportional to the speed of the flow (which is inversely proportional to the section of the channel or vessel). Thus, by miniaturizing the viscosity meter it is possible to obtain at given flow rate forces that are at least as great as for the viscosity meter that was subjected to testing. The quantities of fluids used in a miniaturized device may then be of milliliter (mL) order.

Applications for the miniaturized viscosity meter may be measurements on fluids, possibly non-newtonian fluids, that are expensive or difficult to obtain in large quantities.

The method and the viscosity meter of the invention are intended essentially for measuring the viscosity of liquids.

The method of the invention presents another advantage, namely that of being able to perform measurements continuously and at very short time intervals, thus measuring variation in viscosity. This advantage is essential in certain applications (in particular in processed engineering). In contrast, when using capillary, ball, or cup viscosity meters, continuous measurement is very difficult.

In the experiments that have been undertaken, the response time is about 0.2 seconds. It is found to be limited essentially by the interfacing of the pump and the balance with the control and recording device. Nevertheless, it is entirely possible to increase the rate at which measurements are acquired, and it is entirely possible to interface with a movement table serving to control the movement of the elongate element in the opening of the channel.

In general manner, it is known that the viscosity of certain fluids can vary over time. In the context of the invention, this variation over time can be measured from the moment the fluid is caused to flow.

The invention claimed is:

1. A method of measuring the viscosity of a fluid, the method comprising the following steps:
    a) establishing a flow of said fluid under laminar conditions inside a channel (14, 24) having a longitudinal direction and an opening with a dimension D, which is transverse to the longitudinal direction, an elongate element (12, 22) having a transverse dimension d corresponding to a greatest dimension in a cross section thereof, being placed in said channel substantially along the longitudinal direction thereof and substantially at a center thereof and along the dimension D, a fraction l of the length of the elongate element being immersed in said channel, the ratio D/d being greater than 5;
    b) measuring the friction force (f) exerted by said fluid on the walls of said elongate element;
    c) calculating the dynamic viscosity (TO of said fluid using the following equation:

$$f = \lambda \eta l U \quad (1)$$

where:
    U is the mean speed of the flow; and
    $\lambda$ is a geometrical factor, and wherein steps b) and c) are implemented in succession for different positions of said elongate element in said channel, along the characteristic transverse dimension D.

2. A method according to claim 1, wherein steps a) to c) are implemented for a single value of U, when the fluid is newtonian.

3. A method according to claim 1, wherein steps a) to c) are implemented successively using different values of U, when the fluid is non-newtonian.

4. A method according to claim 1, wherein said method is implemented continuously.

5. A viscosity meter implementing the measurement method according to claim 1, and comprising:
    a channel (14, 24) having a longitudinal direction, a length L and an opening with a dimension D, the dimension D being transverse to the longitudinal direction;
    an elongate element (12, 22) having a transverse dimension d corresponding to a greatest dimension in a cross section thereof, and having an immersed fraction of length l, the ratio D/d being greater than 5, said element being placed in said channel in such a manner as to extend substantially along the longitudinal direction of said channel, substantially at a center of the channel along the dimension D;
    measurement means (13, 23) for measuring the friction force (f) exerted on the walls of said elongate element when a fluid flow is established in said channel and circulates through the opening of said channel and along the length of said channel, and
    means for moving the elongate element in translation in the opening of the channel in order to measure variations in the friction force with the position of said element along the transverse dimension.

6. A viscosity meter according to claim 5, associated with means for causing the fluid to circulate, said means comprising an imposed flow rate pump.

7. A viscosity meter according to claim 6, wherein said channel (14) is defined by the empty space between two substantially parallel plates (10, 11).

8. A viscosity meter according to claim 6, wherein said channel (24) is defined by a cylindrical vessel (20).

9. A viscosity meter according to claim 6, wherein the channel and the elongate element are elements for single use.

10. A viscosity meter according to claim 5, wherein said channel (14) is defined by the empty space between two substantially parallel plates (10, 11).

11. A viscosity meter according to claim 10, wherein the channel and the elongate element are elements for single use.

12. A viscosity meter according to claim 5, wherein said channel (24) is defined by a cylindrical vessel (20).

13. A viscosity meter according to claim 12, wherein the channel and the elongate element are elements for single use.

14. A viscosity meter according to claim 5, wherein the channel and the elongate element are elements for single use.

* * * * *